(12) United States Patent  
Sasamoto et al.

(10) Patent No.: US 9,364,137 B2  
(45) Date of Patent: Jun. 14, 2016

(54) ENDOSCOPE IMAGE-ACQUISITION UNIT AND ENDOSCOPE APPARATUS

(71) Applicant: OLYMPUS CORPORATION, Tokyo (JP)

(72) Inventors: Tsutomu Sasamoto, Tokyo (JP); Keiji Murata, Aichi (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 14/725,611

(22) Filed: May 29, 2015

(65) Prior Publication Data

US 2015/0257631 A1 Sep. 17, 2015

Related U.S. Application Data

(63) Continuation of application No. PCT/JP2014/066365, filed on Jun. 19, 2014.

(30) Foreign Application Priority Data

Jun. 21, 2013 (JP) ................................. 2013-130519

(51) Int. Cl.
| | |
|---|---|
| *A61B 1/00* | (2006.01) |
| *A61B 1/04* | (2006.01) |
| *G02B 7/02* | (2006.01) |
| *G02B 23/24* | (2006.01) |
| *G01J 1/02* | (2006.01) |
| *G01J 1/04* | (2006.01) |

(52) U.S. Cl.
CPC ............ *A61B 1/00128* (2013.01); *A61B 1/0011* (2013.01); *A61B 1/00105* (2013.01); 
(Continued)

(58) Field of Classification Search
CPC ........... A61B 1/00128; A61B 1/00105; A61B 1/00112
USPC ........... 250/216, 239; 600/101, 102, 109, 160
See application file for complete search history.

(56) References Cited

U.S. PATENT DOCUMENTS

| | | | | |
|---|---|---|---|---|
| 4,960,106 A | * | 10/1990 | Kubokawa | ........... A61B 1/0008 600/104 |
| 2007/0276185 A1 | * | 11/2007 | Gono | ................... A61B 1/0008 600/156 |

FOREIGN PATENT DOCUMENTS

| | | |
|---|---|---|
| CN | 101548874 | 10/2009 |
| JP | 01-095174 | 4/1989 |

(Continued)

OTHER PUBLICATIONS

International Search Report, dated Sep. 9, 2014, issued in corresponding International Application No. PCT/JP2014/066365.

*Primary Examiner* — Kevin Pyo
(74) *Attorney, Agent, or Firm* — Kenyon & Kenyon LLP

(57) ABSTRACT

Positioning precision between an image-acquisition device and an objective lens is enhanced by suppressing manufacturing errors. Provided is an endoscope image-acquisition unit equipped with an objective-lens-unit frame that holds an objective lens and an image-acquisition-device holding frame that is fitted to the objective-lens-unit frame and that holds an image-acquisition device, wherein the objective-lens-unit frame and the image-acquisition-device holding frame are attached and secured to each other by means of thermosetting resin that is applied to fitting portions therebetween and in which polar-molecule materials are mixed, and one of the objective-lens-unit frame and the image-acquisition-device holding frame, whichever one is positioned outside at the fitting portions, is formed of a material that allows microwaves to pass therethrough.

6 Claims, 3 Drawing Sheets

(52) U.S. Cl.
CPC ............... *A61B1/00195* (2013.01); *A61B 1/04* (2013.01); *G01J 1/0271* (2013.01); *G01J 1/0411* (2013.01); *G02B 7/02* (2013.01); *G02B 7/025* (2013.01); *G02B 23/243* (2013.01); *G02B 23/2476* (2013.01); *A61B 1/00096* (2013.01)

(56) References Cited

FOREIGN PATENT DOCUMENTS

| JP | 08-073818 | 3/1996 |
|----|-----------|--------|
| JP | 09-192093 | 7/1997 |
| JP | 2002-336190 | 11/2002 |
| JP | 2003-111715 | 4/2003 |
| JP | 2003-230532 | 8/2003 |
| JP | 2005-323874 | 11/2005 |
| JP | 2006-006529 | 1/2006 |
| JP | 2006-143876 | 6/2006 |
| JP | 2006-251272 | 9/2006 |
| JP | 2008-125902 | 6/2008 |
| JP | 2008-156510 | 7/2008 |
| JP | 2009-294496 | 12/2009 |
| JP | 2010-185051 | 8/2010 |
| JP | 2010-269072 | 12/2010 |
| WO | 2010/047396 | 4/2010 |

\* cited by examiner

FIG. 3

| EXAMPLE | P [μm] | Fno | 2.5× P[μm] ×Fno | MATERIAL FOR OBJECTIVE-LENS-UNIT FRAME | MATERIAL FOR IMAGE-ACQUISITION-DEVICE HOLDING FRAME | POLAR MOLECULE | εc | εs | ds [mm] | √εc/√εs×ds [mm] |
|---|---|---|---|---|---|---|---|---|---|---|
| 1 | 1.4 | 4.8 | 0.017 | POLYSULFONE | POLYSULFONE | TITANIUM OXIDE | 83 | 3.1 | 0.2 | 1.035 |
| 2 | 1.3 | 4.5 | 0.015 | STAINLESS STEEL | POLYSULFONE | CARBON BLACK | 12 | 3.1 | 0.2 | 0.393 |
| 3 | 1.1 | 3.8 | 0.010 | POLYSULFONE | POLYSULFONE | CARBON BLACK | 12 | 3.1 | 0.1 | 0.197 |
| 4 | 1.5 | 5.23 | 0.020 | STAINLESS STEEL | POLYSULFONE | TITANIUM DIOXIDE | 110 | 3.1 | 0.4 | 2.383 |
| 5 | 1.2 | 4.19 | 0.013 | POLYSULFONE | POLYSULFONE | IRON OXIDE | 14.2 | 3.1 | 0.4 | 0.856 |
| 6 | 1.6 | 5.58 | 0.022 | POLYSULFONE | POLYSULFONE | ZIRCONIUM OXIDE | 12.5 | 3.1 | 0.05 | 0.100 |
| 7 | 1.7 | 5.93 | 0.025 | STAINLESS STEEL | POLYSULFONE | BARIUM TITANATE | 1200 | 3.1 | 0.7 | 13.772 |
| 8 | 1.55 | 5.4 | 0.021 | POLYSULFONE | POLYSULFONE | POTASSIUM OXIDE | 11.8 | 3.1 | 0.25 | 0.488 |
| 9 | 1.45 | 5.06 | 0.018 | POLYSULFONE | POLYSULFONE | ALUMINUM OXIDE | 9.4 | 3.1 | 0.3 | 0.522 |
| 10 | 1 | 3.5 | 0.009 | PEEK | PEEK | TITANIUM OXIDE | 83 | 3.3 | 0.2 | 1.003 |
| 11 | 1.55 | 5.4 | 0.021 | POLYSULFONE | PEEK | CARBON BLACK | 12 | 3.3 | 0.1 | 0.191 |
| 12 | 1.35 | 4.71 | 0.016 | POLYSULFONE | PEEK | CARBON BLACK | 12 | 3.3 | 0.05 | 0.095 |
| 13 | 1.25 | 4.36 | 0.014 | PEEK | PEEK | TITANIUM DIOXIDE | 110 | 3.3 | 0.4 | 2.309 |
| 14 | 1.15 | 4.01 | 0.012 | STAINLESS STEEL | PEEK | IRON OXIDE | 14.2 | 3.3 | 0.4 | 0.830 |
| 15 | 1.2 | 4.19 | 0.013 | PEEK | PEEK | ZIRCONIUM OXIDE | 12.5 | 3.3 | 0.05 | 0.097 |
| 16 | 1.3 | 4.52 | 0.015 | PEEK | PEEK | BARIUM TITANATE | 1200 | 3.3 | 0.6 | 11.442 |
| 17 | 1.5 | 5.23 | 0.020 | POLYSULFONE | PEEK | POTASSIUM OXIDE | 11.8 | 3.3 | 0.25 | 0.473 |
| 18 | 1.6 | 5.58 | 0.022 | POLYSULFONE | PEEK | ALUMINUM OXIDE | 9.4 | 3.3 | 0.3 | 0.506 |
| 19 | 1.45 | 5.06 | 0.018 | POLYCARBONATE | POLYCARBONATE | TITANIUM OXIDE | 83 | 2.9 | 0.15 | 0.802 |
| 20 | 1.3 | 4.5 | 0.015 | POLYSULFONE | POLYCARBONATE | CARBON BLACK | 12 | 2.9 | 0.1 | 0.203 |
| 21 | 1.05 | 3.66 | 0.010 | PEEK | POLYCARBONATE | CARBON BLACK | 12 | 2.9 | 0.2 | 0.407 |
| 22 | 1.65 | 5.76 | 0.024 | STAINLESS STEEL | POLYCARBONATE | TITANIUM DIOXIDE | 110 | 2.9 | 0.5 | 3.079 |
| 23 | 1.51 | 5.27 | 0.020 | POLYCARBONATE | POLYCARBONATE | IRON OXIDE | 14.2 | 2.9 | 0.3 | 0.664 |
| 24 | 1.72 | 6 | 0.026 | STAINLESS STEEL | POLYCARBONATE | ZIRCONIUM OXIDE | 12.5 | 2.9 | 0.05 | 0.104 |
| 25 | 1.34 | 4.67 | 0.016 | POLYCARBONATE | POLYCARBONATE | BARIUM TITANATE | 1200 | 2.9 | 0.8 | 16.274 |
| 26 | 1.34 | 4.67 | 0.016 | POLYCARBONATE | POLYCARBONATE | POTASSIUM OXIDE | 11.8 | 2.9 | 0.25 | 0.504 |
| 27 | 1.34 | 4.67 | 0.016 | POLYSULFONE | POLYCARBONATE | ALUMINUM OXIDE | 9.4 | 2.9 | 0.3 | 0.540 |

ENDOSCOPE IMAGE-ACQUISITION UNIT AND ENDOSCOPE APPARATUS

CROSS-REFERENCE TO RELATED APPLICATIONS

This is a continuation of International Application PCT/JP2014/066365, with an international filing date of Jun. 19, 2014, which is hereby incorporated by reference herein in its entirety. This application claims the benefit of Japanese Patent Application No. 2013-130519, the content of which is incorporated herein by reference.

TECHNICAL FIELD

The present invention relates to an image-acquisition unit employed in an endoscope and to an endoscope apparatus provided with this image-acquisition unit.

BACKGROUND ART

In medical endoscopes such as nasal endoscopes or the like, there has been a demand in recent years for reducing the size of a tip of an inserted portion thereof from the viewpoint of reducing the burden on patients or the like. In response, small image-acquisition devices (CCDs, and CMOSs) have been developed for endoscopes, and the pixel pitch thereof is also decreasing year by year. Associated with this decrease in the pixel pitch, allowable assembly errors between individual lenses, between an image-acquisition device and an objective lens, and so forth are also decreasing, and thus, assembly errors of several micrometers are becoming problematic.

As disclosed in Patent Literature 1, an endoscope image-acquisition unit has a structure in which an objective-lens-unit frame that holds an objective lens and an image-acquisition-device holding frame that holds an image-acquisition device are fitted together. More specifically, thermosetting resin is filled in fitting portions between the objective-lens-unit frame and the image-acquisition-device holding frame, and, after the positions of an objective optical system and the image-acquisition device are set, the objective-lens-unit frame and the image-acquisition-device holding frame are secured by using assembly jigs and are placed in a drying oven or the like in this state to be heated. By doing so, the thermosetting resin is hardened, thus attaching and securing the objective-lens-unit frame to the image-acquisition-device holding frame.

CITATION LIST

Patent Literature

{Patent Literature 1} Japanese Unexamined Patent Application, Publication No. Hei 9-192093

SUMMARY OF INVENTION

Technical Problem

In the endoscope image-acquisition unit of the related art described above, when hardening the thermosetting resin, because the objective-lens-unit frame and the image-acquisition-device holding frame are heated in the drying oven in a state in which they are secured by using the assembly jigs, thermal expansion occurs in components thereof and the jigs. Due to this thermal expansion, the objective-lens-unit frame and the image-acquisition-device holding frame shift from a desired position, and thus, there is a possibility of causing a manufacturing error that exceeds the tolerances.

Solution to Problem

An aspect of the present invention provides an endoscope image-acquisition unit including an objective-lens-unit frame that holds an objective lens; and an image-acquisition-device holding frame that is fitted to the objective-lens-unit frame and that holds an image-acquisition device, wherein the objective-lens-unit frame and the image-acquisition-device holding frame are attached and secured to each other by means of thermosetting resin that is applied to fitting portions therebetween and in which polar-molecule materials are mixed, and one of the objective-lens-unit frame and the image-acquisition-device holding frame, whichever one is positioned outside at the fitting portions, is formed of a material that allows microwaves to pass therethrough.

In the above-described aspect, it is preferable that the following Conditional Expression (1) be satisfied.

$$2.5 \times P[\mu m] \times Fno < 0.03 \tag{1}$$

where P is the pitch of the image-acquisition device, and Fno is an effective F number of the objective lens.

In the above-described aspect, it is preferable that the following Conditional Expression (2) be satisfied.

$$\{Eq. 1\}$$

$$0.09 < \frac{\sqrt{\varepsilon c}}{\sqrt{\varepsilon s}} \times ds[mm] < 20 \tag{2}$$

Note that $\varepsilon c$ is the permittivity of a material having the highest permittivity among the polar-molecule materials mixed in the thermosetting resin, $\varepsilon s$ is the permittivity of a material that forms the frame which is positioned outside when the objective-lens-unit frame and the image-acquisition-device holding frame are fitted together, and ds is the thickness of the frame material for the frame positioned outside, which is measured perpendicularly to an attaching surface.

In the above-described aspect, it is preferable that the polar-molecule materials include at least one of titanium oxide, titanium dioxide, magnesium oxide, potassium oxide, zirconium oxide, iron oxide, aluminum oxide, carbon black, and barium titanate.

In addition, in the above-described aspect, it is preferable that the material that allows microwaves to pass therethrough be any one of polysulfone, PMMA, PEEK, polyamide, polyimide, and ceramic.

In addition, another aspect of the present invention provides an endoscope apparatus provided with an endoscope image-acquisition unit according to the aspect described above.

BRIEF DESCRIPTION OF DRAWINGS

FIG. 3 is a table showing values that Conditional Expressions take in individual examples according to the embodiment of the present invention.

DESCRIPTION OF EMBODIMENT

An endoscope image-acquisition unit according to an embodiment of the present invention will be described below with reference to the drawings.

Figure 1:
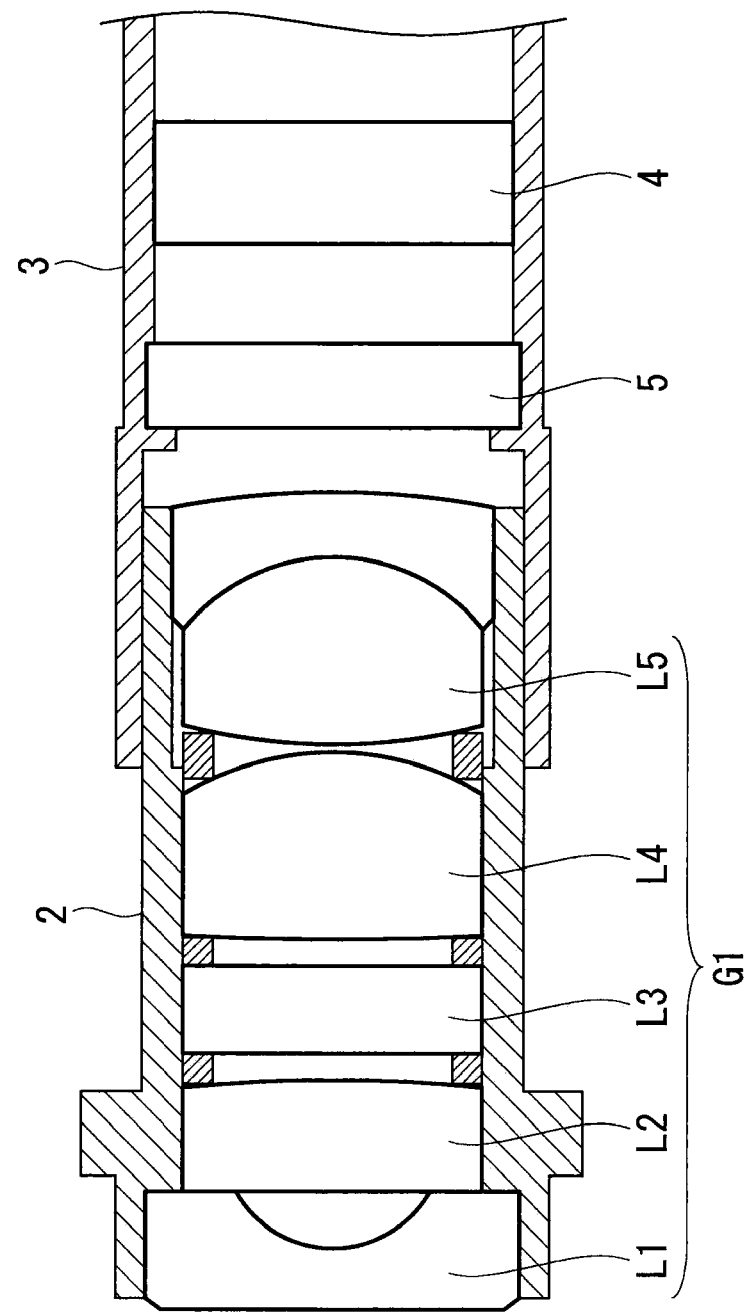
FIG. 1 is a cross-sectional view showing the overall configuration of an endoscope image-acquisition unit according to an embodiment of the present invention.

An endoscope image-acquisition unit 1 according to this embodiment shown in FIG. 1 is provided with an objective-lens-unit frame 2 that holds an objective lens and an image-acquisition-device holding frame 3 that is fitted to the objective-lens-unit frame 2 and that holds an image-acquisition device.

The objective-lens-unit frame 2 holds a lens group G1 formed of a plurality of objective lenses L1, L2, L3, L4, and L5.

The image-acquisition-device holding frame 3 holds an image-acquisition device 4 and a cover glass 5. In addition, the image-acquisition-device holding frame 3 is formed of polysulfone so as to allow microwaves to pass therethrough. Note that the material that forms the image-acquisition-device holding frame 3 is not limited to polysulfone so long as the material allows microwaves to pass therethrough. Therefore, for example, PMMA, PEEK, polyamide, polyimide, ceramic, or the like can be employed. By doing so, because at least the frame positioned outside when the objective-lens-unit frame and the image-acquisition-device holding frame are fitted together is prevented from expanding and causing a positional shift when heated, it is possible to enhance the positioning precision between the image-acquisition device and the objective lens.

The objective-lens-unit frame 2 and the image-acquisition-device holding frame 3 are configured so as to be fitted together at predetermined areas on the image side of the objective-lens-unit frame 2 and the object side of the image-acquisition-device holding frame 3, and thermosetting resin (not shown) that serves as an adhesive is applied to these fitting portions, and so that the objective-lens-unit frame 2 and the image-acquisition-device holding frame 3 are secured.

In the thermosetting resin, at least one type of polar-molecule material, for example, titanium oxide, titanium dioxide, magnesium oxide, potassium oxide, zirconium oxide, iron oxide, aluminum oxide, carbon black, barium titanate, or the like, is mixed therein. By doing so, the thermosetting resin is heated and hardened by means of microwaves or electromagnetic induction, and thus, it is possible to enhance the positioning precision between the image-acquisition device and the objective lens. In the following description of this embodiment, the thermosetting resin will be described assuming that titanium oxide is mixed therein.

With this aspect, the thermosetting resin in which the polar-molecule material is mixed is applied to the fitting portions between the objective-lens-unit frame and the image-acquisition-device holding frame, and at least the frame positioned outside when the objective-lens-unit frame and the image-acquisition-device holding frame are fitted together is formed of the material that allows microwaves to pass therethrough. Because of this, after setting the positions of the objective-lens-unit frame and the image-acquisition-device holding frame, that is to say, after setting the positions of the objective lens and the image-acquisition device, the polar-molecule material is made to vibrate by heating by means of microwaves, electromagnetic induction, or the like, and thus, it is possible to gradually heat and harden the thermosetting resin via the polar-molecule materials.

As above, when hardening the thermosetting resin, because it suffices just to irradiate the thermosetting resin with microwaves or to apply induction heating thereto, the assembly jigs are not heated, and, in addition, at least the frame positioned outside is not heated by microwaves.

Therefore, it is not necessary to take into consideration positional shifts due to the thermal expansion of the jigs and the components, and it is possible to enhance the positioning precision between the image-acquisition device and the objective lens by suppressing manufacturing errors.

The above aspect affords an advantage in that it is possible to enhance positioning precision between an image-acquisition device and an objective lens by suppressing manufacturing errors.

In addition, the endoscope image-acquisition unit 1 is configured so as to satisfy the following Conditional Expression (1).

$$2.5 \times P[\mu m] \times Fno < 0.03 \quad (1)$$

where P is the pitch of the image-acquisition device, and Fno is an effective F number of the objective lens.

Figure 2:
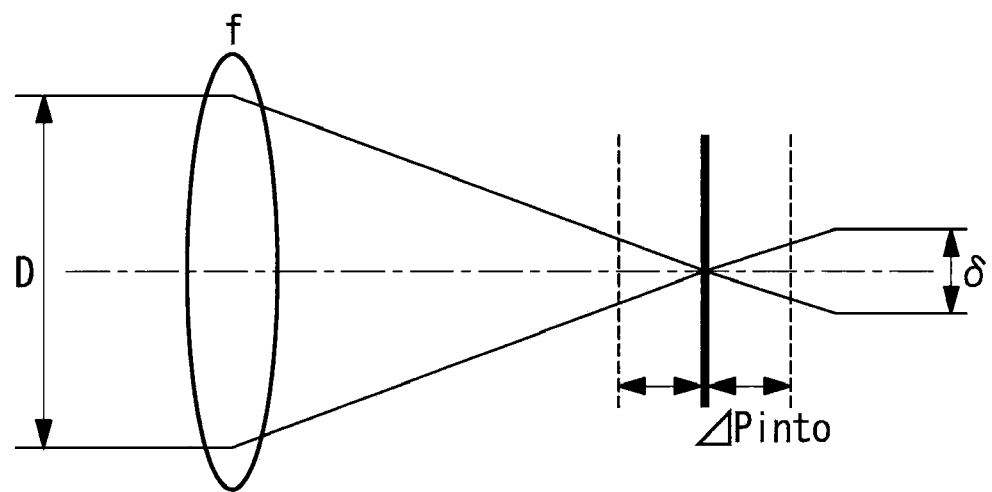
FIG. 2 is a diagram for explaining an objective lens, a focal length, and a focus-shift tolerance in the endoscope image-acquisition unit according to the embodiment of the present invention.

This configuration is employed because, when $\Delta_{Pinto}$ is assumed to be the focus-shift tolerances of the endoscope image-acquisition unit 1, as shown in FIG. 2, $$\delta/D = \Delta_{Pinto}/f$$

$$\Delta_{Pinto} = \delta \cdot f/D$$

holds, and therefore, when $$\delta = 2.5P,$$

$$\Delta_{Pinto} = Fno \times 2.5 \times P$$

is obtained,
where D is the effective diameter of an objective lens, f is the focal length, and δ is a blur diameter allowed in an image.

Even in an optical system requiring high-precision positioning that satisfies the above-described Conditional Expression (1), it is possible to enhance the positioning precision.

Note that, in this embodiment, δ is set to 2.5P for the following reasons. Specifically, in the case in which, in each pixel of the image-acquisition device, a monochromatic chart is imaged by using the image-acquisition device in the objective optical system, a reference blur level is δ=2P. Image-acquisition devices employing such a reference level include image-acquisition devices that use luminance signals. In addition, in image-acquisition devices that are provided with color filters for individual pixels of the image-acquisition device, it is necessary to create luminance signals based on the color filters, and, in general, the reference blur level is considered to be at a level of δ=3P. Therefore, as a reference blur level compatible with all types of image-acquisition devices, an intermediate value, δ=2.5P, is employed.

In addition, the endoscope image-acquisition unit 1 is configured so as to satisfy the following Conditional Expression (2).

{Eq. 2}

$$0.09 < \frac{\sqrt{\varepsilon c}}{\sqrt{\varepsilon s}} \times ds[mm] < 20 \quad (2)$$

Note that εc is the permittivity of the material having the highest permittivity among the polar-molecule materials mixed in the thermosetting resin, ϵs is the permittivity of a material that forms the image-acquisition-device holding frame which is positioned outside when the objective-lens-unit frame and the image-acquisition-device holding frame are fitted together, and ds is the thickness of the frame material for the image-acquisition-device holding frame positioned outside, which is measured perpendicularly to the attaching surface.

In the case of heating by means of microwaves or heating by means of electromagnetic induction, when the upper limit of this Conditional Expression (2) is exceeded, size reduction of the endoscope image-acquisition unit is hindered because the size of the heating apparatus increases and causes interference with jigs or the like that are used when manufacturing the endoscope image-acquisition unit.

In addition, when Conditional Expression (2) falls below the lower limit thereof, when heating, there is a risk of failing to heat the thermosetting resin to the temperature needed to harden the thermosetting resin.

Therefore, by satisfying Conditional Expression (2), it is possible to perform sufficient heating by means of microwaves or electromagnetic induction without increasing the size of a heating apparatus.

In other words, it is possible to enhance the positioning precision between the image-acquisition device and the objective lens without increasing the size of a heating apparatus while performing sufficient heating when heating by means of microwaves or electromagnetic induction.

Note that it is preferable that ds be a value between 0.05 and 1 mm. This is because, from the viewpoint of processing, setting the thickness too low makes processing impossible and, also, increasing the thickness makes the endoscope itself large. In this embodiment, assuming that the thickness of the frame material for the image-acquisition-device holding frame 3, which is measured perpendicularly to the attaching surface, is set to be ds=0.2 mm, because the permittivity of titanium oxide, which is a polar-molecule material, is ϵc=83 and the permittivity of polysulfone, which is the material forming the image-acquisition-device holding frame, is ϵs=3.1, the following Conditional Expression (3) holds.

{Eq. 3}

$$\frac{\sqrt{\varepsilon c}}{\sqrt{\varepsilon s}} \times ds[\text{mm}] = 1.035 \qquad (3)$$

FIG. 3 lists, as examples 1 to 27, endoscope image-acquisition units configured by appropriately selecting the objective-lens-unit frame 2, the image-acquisition-device holding frame 3, and the polar-molecule materials, and shows values for Conditional Expressions (1) and (2), described above, for the individual examples.

Note that, in this embodiment described above and the individual examples in FIG. 3, examples in which the image-acquisition-device holding frame 3 is positioned outside when the objective-lens-unit frame 2 and the image-acquisition-device holding frame 3 are fitted together have been described; however, there is no limitation thereto, and the objective-lens-unit frame 2 may be positioned outside.

In addition, not only the material of the frame positioned outside when the objective-lens-unit frame 2 and the image-acquisition-device holding frame 3 are fitted together, but also the material of the frame positioned inside may be a material that allows microwaves to pass therethrough. Specifically, both the objective-lens-unit frame and the image-acquisition-device holding frame may be formed of a material that allows microwaves to pass therethrough.

With this embodiment, the thermosetting resin in which the polar-molecule material is mixed is applied to the fitting portions between the objective-lens-unit frame 2 and the image-acquisition-device holding frame 3, and they are attached and secured to each other by this thermosetting resin.

Because of this, after setting the positions of the objective-lens-unit frame and the image-acquisition-device holding frame, that is to say, after setting the positions of the objective lens and the image-acquisition device, the polar-molecule material is made to vibrate by heating the fitting portions by means of externally applied microwaves, electromagnetic induction, or the like. Frictional heat is generated by the vibrations of the polar-molecule material, and, by doing so, it is possible to heat and harden only the thermosetting resin.

As above, when hardening the thermosetting resin, it suffices just to irradiate the thermosetting resin with microwaves or to apply induction heating thereto, and, because the thermosetting resin can be heated without having to place the components in a drying oven or the like in a state in which assembly jigs are attached thereto, the assembly jigs are not heated.

In addition, because at least the frame positioned outside when the objective-lens-unit frame and the image-acquisition-device holding frame are fitted together is formed of the material that allows microwaves to pass therethrough, this frame is not heated by microwaves when the frames are heated; that is to say, a positional shift due to expansion of this frame does not occur.

Therefore, it is not necessary to take into consideration positional shifts of the thermal expansion of the jigs and the components, and it is possible to enhance the positioning precision between the objective lens and the image-acquisition device by suppressing manufacturing errors.

REFERENCE SIGNS LIST

1 endoscope image-acquisition unit
2 objective-lens-unit frame
3 image-acquisition-device holding frame
4 image-acquisition device
5 cover glass
G1 lens group
L1 objective lens
L2 objective lens
L3 objective lens
L4 objective lens
L5 objective lens

The invention claimed is:

1. An endoscope image-acquisition unit comprising:
    an objective-lens-unit frame that holds an objective lens; and
    an image-acquisition-device holding frame that is fitted to the objective-lens-unit frame and that holds an image-acquisition device, wherein
    the objective-lens-unit frame and the image-acquisition-device holding frame are attached and secured to each other by means of thermosetting resin that is applied to fitting portions therebetween and in which polar-molecule materials are mixed, and
    one of the objective-lens-unit frame and the image-acquisition-device holding frame, whichever one is positioned outside at the fitting portions, is formed of a material that allows microwaves to pass therethrough.

2. An endoscope image-acquisition unit according to claim 1, wherein Conditional Expression (1) below is satisfied:

$$2.5 \times P[\mu m] \times Fno < 0.03 \tag{1}$$

where P is a pitch of the image-acquisition device, and Fno is an effective F number of the objective lens.

3. An endoscope image-acquisition unit according to claim 1, wherein following Conditional Expression (2) below is satisfied:

{Eq. 1}

$$0.09 < \frac{\sqrt{\varepsilon c}}{\sqrt{\varepsilon s}} \times ds[mm] < 20 \tag{2}$$

where $\varepsilon c$ is a permittivity of a material having the highest permittivity among the polar-molecule materials mixed in the thermosetting resin, $\varepsilon s$ is a permittivity of a material that forms the frame which is positioned outside when the objective-lens-unit frame and the image-acquisition-device holding frame are fitted together, and ds is a thickness of the frame material for the frame positioned outside, which is measured perpendicularly to an attaching surface.

4. An endoscope image-acquisition unit according to claim 1, wherein the polar-molecule materials include at least one of titanium oxide, titanium dioxide, magnesium oxide, potassium oxide, zirconium oxide, iron oxide, aluminum oxide, carbon black, and barium titanate.

5. An endoscope image-acquisition unit according to claim 1, wherein the material that allows microwaves to pass therethrough is any one of polysulfone, PMMA, PEEK, polyamide, polyimide, and ceramic.

6. An endoscope apparatus comprising:
an endoscope image-acquisition unit according to of claim 1.

* * * * *